United States Patent [19]
Wertheimer

[11] 4,052,600
[45] Oct. 4, 1977

[54] MEASUREMENT OF STATISTICAL PARAMETERS OF A DISTRIBUTION OF SUSPENDED PARTICLES

[75] Inventor: Alan L. Wertheimer, North Wales, Pa.

[73] Assignee: Leeds & Northrup Company, North Wales, Pa.

[21] Appl. No.: 538,382

[22] Filed: Jan. 6, 1975

[51] Int. Cl.$^2$ .................. G01N 21/00; G06F 15/20; G02B 5/20
[52] U.S. Cl. .................. 364/554; 356/102; 356/103; 350/162 SF; 364/525
[58] Field of Search .................. 235/151.3, 92 PC; 356/103, 102; 350/162 R, 162 SF

[56] References Cited

U.S. PATENT DOCUMENTS

| | | | |
|---|---|---|---|
| 3,488,106 | 1/1970 | Lohmann | 350/162 R |
| 3,612,689 | 10/1971 | Liskowitz | 356/103 |
| 3,809,478 | 5/1974 | Talbot | 356/102 X |
| 3,830,569 | 8/1974 | Meric | 356/102 X |
| 3,835,315 | 9/1974 | Gravitt, Jr. | 356/103 X |
| 3,869,208 | 3/1975 | Lorenz | 356/103 X |
| 3,873,206 | 3/1975 | Wilcock | 356/103 |

Primary Examiner—Edward J. Wise
Attorney, Agent, or Firm—William G. Miller, Jr.; Raymond F. MacKay

[57] ABSTRACT

A rotating mask having three spatial filters is placed in the light path after a laser beam is passed through a sample having a collection of particles. The mask sequentially filters the light scattered by each particle to produce at a detector receiving the filtered light a response which is in accordance with the second, third and fourth power of the particle diameter. The detector integrates the response to all particles in the laser beam and the signal resulting from the integration of the response due to the individual filters is used to calculate statistical parameters. The mean of the area distribution is calculated as the third power response divided by the second power response. The mean of the volume distribution is calculated as the fourth power response divided by the third power response and the standard deviation of the area distribution as the square root of the product of the mean of the area distribution and the difference between the mean of the volume distribution and the mean of the area distribution.

5 Claims, 3 Drawing Figures

MEASUREMENT OF STATISTICAL PARAMETERS OF A DISTRIBUTION OF SUSPENDED PARTICLES

BACKGROUND OF THE INVENTION

This invention relates to a method and means for measuring certain parameters of the statistical distribution of a collection of particles. More particularly the invention relates to the measurement of the mean of the area distribution, the mean of the volume distribution, and the standard deviation of the area distribution of the particles.

This invention has usefulness in the measurement of the three above mentioned statistical parameters in a number of applications. For example, it would be useful in measuring the progress of the finish grinding of Taconite ore or cement, also in explosion hazard monitoring and dust respiration measurements as well as in measurements of bacteriologicals.

There has previously been developed a method and means for measuring the total particle volume or mass by the use of a monochromatic laser light beam directed through a collection of particles and then through a spatial filter which serves to establish a third power relationship between the diffracted light flux from each particle transmitted by the spatial filter and the radius of the particle. In this connection reference should be made to U.S. patent application Ser. No. 403,288 of William Leslie Wilcock, filed Oct. 3, 1973.

Other prior art devices have utilized computation of distribution data by the use of digital computers in systems which laboriously examine individual particles from the collection to be analyzed and use counting procedures to obtain statistics on the aggregate collection.

The method and means of this invention, like that of Wilcock relies on the fact that the total flux diffracted by a particle (the forward scattered light) is proportional to the square of the particle diameter while the angular scale of the Fraunhofer interference pattern in the Fourier or Fraunhofer plane of the lens collecting the diffracted light is proportional to the reciprocal of the particle diameter in such a way that the proportionality of the total diffracted flux to particle diameter varies from a fourth power relationship near the center of the pattern to a second power relationship for the whole pattern. Thus it is possible, as has been demonstrated by Wilcock, to use a spatial filter in the Fraunhofer plane such that the transmissivity of the filter changes as a function of radius or distance from the optical axis so that the total flux transmitted by the filter is proportional to any power of the particle radius from the second power to and including the fourth power.

It is an object of this invention to provide a method and means for measuring the mean of the particle distribution by area, the mean of the particle distribution by volume and the standard deviation of the area distribution by the use of spatial filters of the type taught by Wilcock.

SUMMARY OF THE INVENTION

In carrying out this invention there is provided means for performing the method for measuring the means of the area distribution, the mean of the volume distribution, and the standard deviation of the area distribution of a collection of particles by steps which include passing a light beam through the collection of particles. The light diffracted from the particles is filtered through a first spatial filter which transmits a proportion of the light flux diffracted from each particle which is proportional to the second power of the radius of that particle. Similarly, a second spatial filter transmits light flux from each particle proportional to the third power of the particle radius and a third spatial filter transmits light flux proportional to the fourth power of the particle radius. There is then produced a first, second and third signal ($X_2$, $X_3$, and $X_4$, respectively) in response to the total integral of the light flux detected passing through the first, second, and third spatial filters due to all of the particles in the collection.

From the signals $X_2$, $X_3$, and $X_4$ there is calculated the mean of the area distribution ($M_A$) as a number proportional to $X_3/X_2$ and the mean of the volume distribution ($M_v$) as a number proportional to the ratio $X_4/X_3$. Using $M_A$ and $M_v$ the standard deviation of the area distribution is then calculated as $M_A(M_v - M_A)$.

DESCRIPTION OF THE PREFERRED EMBODIMENT

Figure 1:
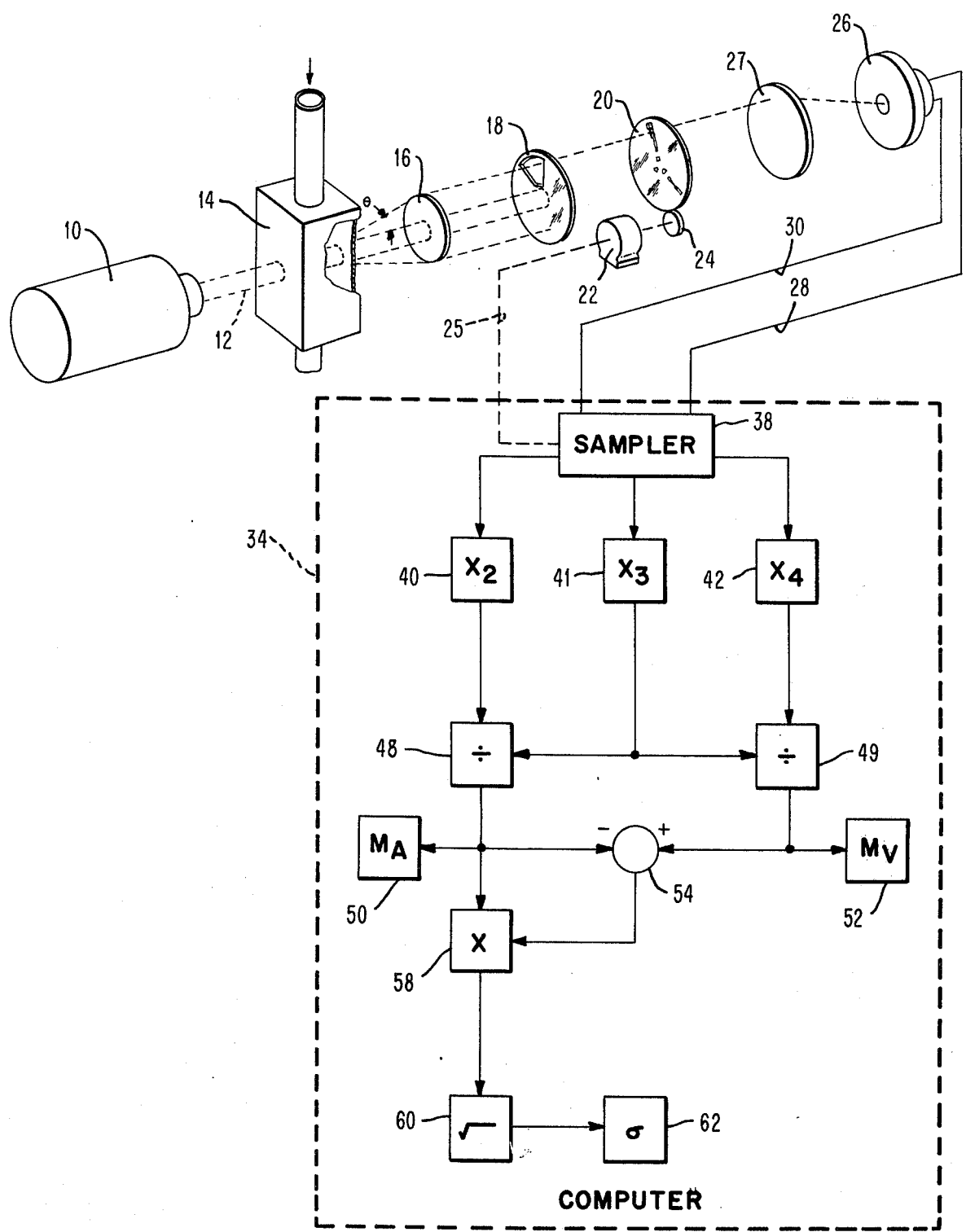
FIG. 1 is a diagram, partially in block form, of the system of the invention.

In FIG. 1 a light source, shown as a laser 10, provides a monochromatic light beam 12. The light beam is directed through a sample region 14 which contains the collection of particles whose statistical parameters are to be measured. The sample region may be a chamber through which there is a constantly flowing sample of fluid suspended particles, for example, or it may be a sample comprised of a fixed collection. In some circumstances the particle collection may consist of a planar sample of particles or a photographic image of them.

The light from the laser will be diffracted by the particles in the collection and the diffracted light from each particle will be concentrated predominantly within an angular extent, $\theta$, which is inversely related to the diameter of the particle.

The light diffracted from the particles is collected by collecting lens 16 and all but a fraction of that light passed by lens 16 is blocked by stationary chopping blade 18. As shown, the chopping blade allows the light to go through a sector spanning an angle of approximately 45° in the plane of the chopping blade which is normal to the optical axis 12. Thus diffracted light is allowed to go through only one of the spatial filters of the rotating mask 20 at any particular time. The chopping blade 18 and mask 20 are closely spaced, the spacing shown in FIG. 1 being for clarity of the drawing only.

Figure 2:
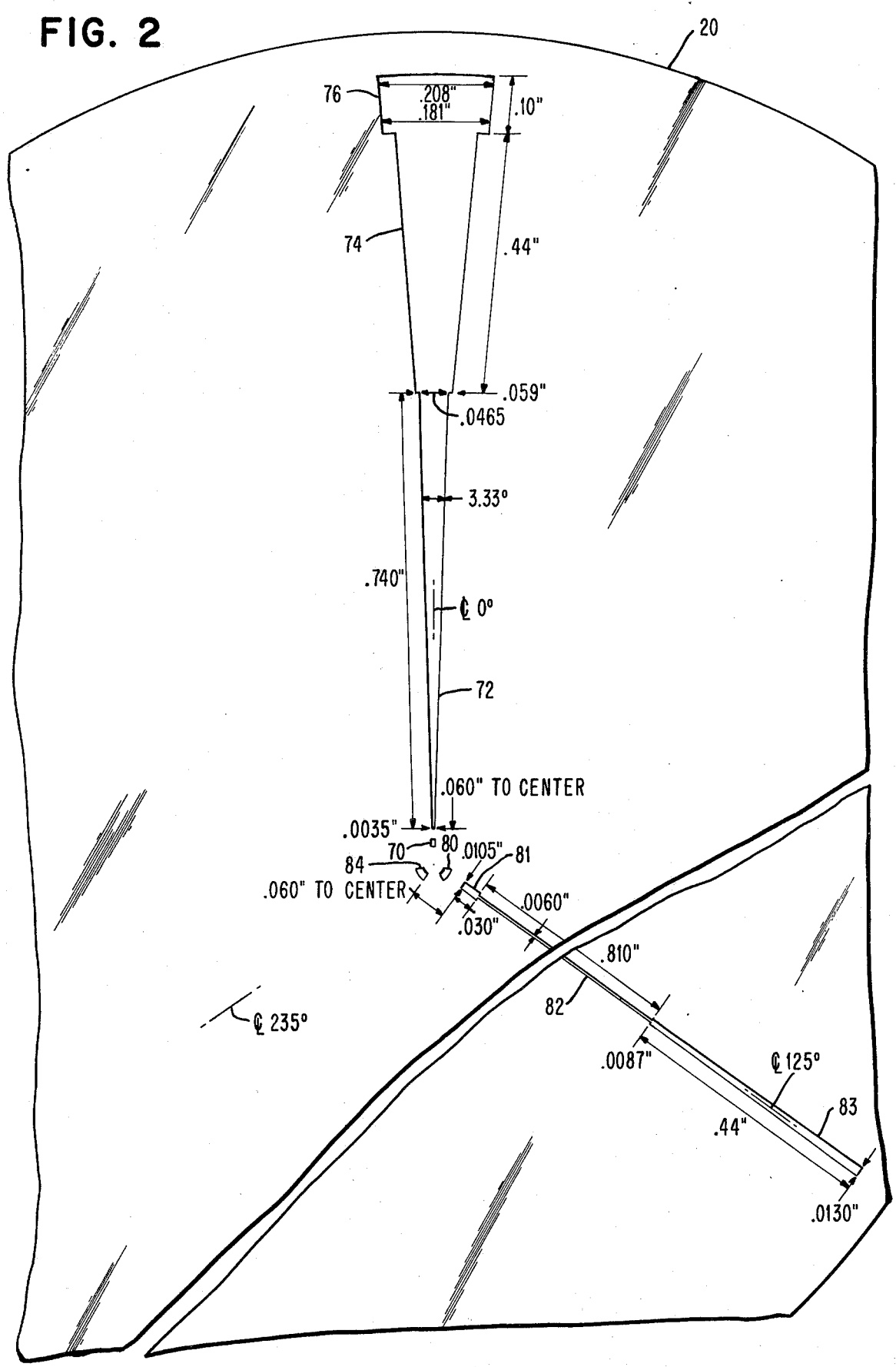
FIG. 2 is a drawing of one form for the spatial filters of the rotating mask of FIG. 1.
Figure 3:
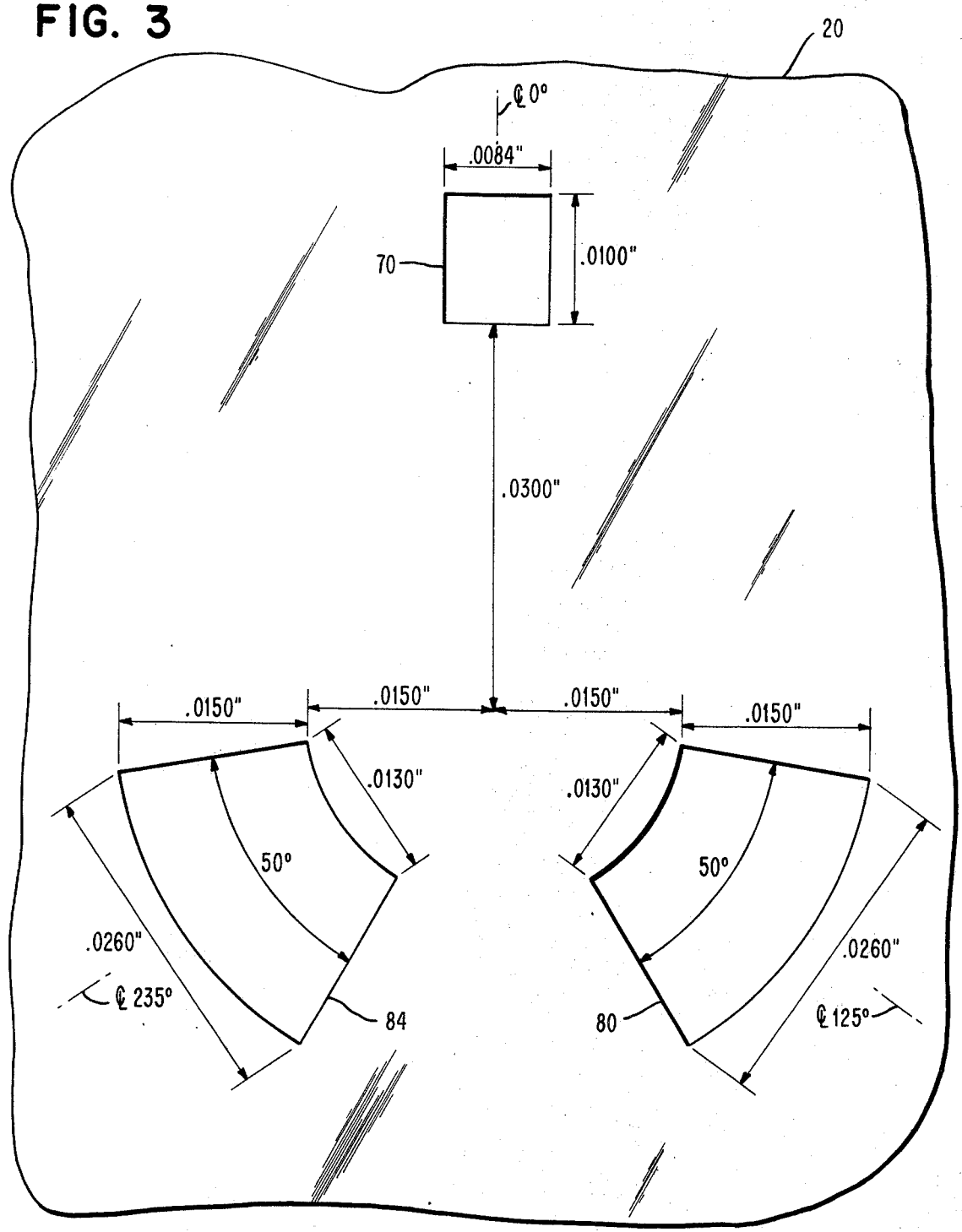
FIG. 3 is an expanded drawing of that part of FIG. 2 which is close to the optical axis.

The mask 20 is located in the Fraunhofer plane of lens 16 and has three spatial filters oriented approximately 120° apart from one another. One form for the rotating mask may be as shown in FIGS. 2 and 3, where the three separate spatial filters provide a second power, third power and fourth power relationship between the flux passed by the filter and the radius of the particle diffracting the flux. The mask 20 is shown in FIG. 1 as being rotated by a motor 22 through a friction drive element 24.

The diffracted light that passes the transparent or open sector of the chopping blade and passes through the spatial filter exposed by the chopping blade at a particular time is directed onto the detector 26 by the field lens 27. The detector then produces a signal output on lines 28 and 30 which is directly related to the total amount of light flux passed by the spatial filter. Thus, if the second power filter is exposed, the signal output is $X_2$, whereas the third power and fourth power filters produce the signal outputs $X_3$ and $X_4$, respectively.

Normally the collection of particles through which the light beam is directed consists of many particles of varying size. The statistical distribution of the particles by number is $D_n(R)$ where $D_n$ represents the number of particles which are present between the radius of R and R+dR. The total flux, X, is the integral of the product of the distribution, $D_n$, and the flux per particle F(R), or $$X_i = \int D_n(R) F_i(R) dR \quad (1)$$

The subscript $i$ indicates the various responses which can be achieved by using the different filters or mask shapes.

Since we are here concerned with the second, third, and fourth power filters the three responses of interest are $$F_2(R) = C_2 R^2 \quad (2)$$

$$F_3(R) = C_3 R^3 \quad (3)$$

$$F_4(R) = C_4 R^4 \quad (4)$$

where $C_2$, $C_3$ and $C_4$ are constants.

$F_2(R)$, for example, specifies that the flux reaching the detector 26 due to each particle of the collection is proportional to the second power of the radius of that particle, $F_3(R)$ and $F_4(R)$ then are proportional to the third and fourth power, respectively.

If $D_n(R)$ is the statistical distribution by number, then $\pi R^2 D_n(R)$ is the distribution by area and $4/3 \pi R^3 D_n(R)$ is the distribution by volume.

The first moment (the mean) of the area distribution is defined as $$M_A = \frac{\int \pi R^2 D_n(R) R \, dR}{\int \pi R^2 D_n(R) \, dR} \quad (5)$$

Similarly the first moment (the mean) of the volume distribution is $$M_v = \frac{\int 4\pi/3 \, R^3 D_n(R) R \, dR}{\int 4\pi/3 \, R^3 D_n(R) \, dR} \quad (6)$$

The standard deviation of the area distribution is defined as $$\sigma A = [M_{2A} - M_A^2]^{1/2} \quad (7)$$

where $M_{2A}$ is the second moment of the area distribution and is defined as $$M_{2A} = \frac{\int \pi R^2 D_n(R) R^2 \, dR}{\int \pi R^2 D_n(R) \, dR} \quad (8)$$

The response functions, $F_i(R)$, as listed in equations 2, 3 and 4, provide the necessary weighting functions to calculate the second, third and fourth power. Upon substitution of equations (2), (3) and (4) into general equation (1) the parameters $M_A$, $M_v$, and $\sigma_A$ are produced as follows $$M_A = C_2 X_3 / C_3 X_2 \quad (9)$$

$$M_v = C_3 X_4 / C_4 X_3 \quad (10)$$

$$\sigma_A = [C_2 X_4 / C_4 X_2 - (C_2 X_3 / C_3 X_2)^2]^{1/2} \quad (11)$$

Finally, since the product of equations (9) and (10) is equivalent to the first term of the bracketed expression in equation (11), $\sigma_A$ can be written as $$\sigma_A = [C_2 X_3 / C_3 X_2 (C_3 X_4 / C_4 X_3 - C_2 X_3 / C_3 X_2)]^{1/2} \quad (12)$$

Therefore $$\sigma_A = [M_A (M_v - M_A)]^{1/2} \quad (13)$$

and it is not necessary to calculate the second moment of equation (8).

To calculate $M_A$, $M_v$ and $\sigma_A$, a computer 34 is connected in FIG. 1 to receive the signals $X_2$, $X_3$, and $X_4$ from the detector 26 over lines 28 and 30. The computer may desirably be a digital computer, however, an analog computer would also adequately do the necessary calculations. For purposes of description the computer block 34 in FIG. 1 is shown with the several functions it must perform laid out as a block diagram as might be used to describe an analog computer.

Initially the incoming signals from lines 28 and 30 must be sequentially sampled by sampler 38 as mask 20 is rotated by motor 22 and friction drive 24. The sampler 38 is operated in synchronism with the rotation of mask 20 through the connection to 24 by shaft 25. The sampler, for example, could be a simple rotary selector switch. Sampler 38 directs the signals $X_2$, $X_3$ and $X_4$ to the separate registers or storage elements 40, 41, and 42 so that they retain the respective signals $X_2$, $X_3$, and $X_4$. Normally those values are measured sequentially and summed over a predetermined time so that ratios calculated from the resulting $X_2$, $X_3$ and $X_4$ stored by the registers at the end of that period represent ratios of average values for those signals during the period, the registers being arranged to accumulate a running total during the period which can be considered to represent the average value. It is, of course, necessary to synchronize the reception of a particular signal with the sending of it to the register reserved for accumulating its value. After the accumulated values have been determined they are used for calculation. Thus, $X_3$ is divided by $X_2$ in block 48 and multiplied by the constant C2/C3 to give $M_A$. $X_4$ is divided by $X_3$ in block 49 and multiplied by the constant C3/C4 to give $M_v$. Both $M_A$ and $M_v$ are displayed in the respective display devices 50 and 52.

$M_A$ is subtracted from $M_v$ in block 54 and the difference is multiplied by $M_A$ in block 58. The resulting quantity $M_A (M_v - M_A)$ is then fed to block 60 where the square root of that quantity is calculated. The square root is then displayed on display device 62 as $\sigma$.

FIG. 2 shows one form for the mask 20. About the 0° center line there is shown the outline of the transparent portion of the spatial filter in the opaque body of mask 20 which provides the second power response to the particle radius to give the signal $X_2$ from detector 26 when the sector exposed to the diffracted light by the chopping blade 18 includes the 0° filter.

The shapes for the filters are generally defined by the function $T(\theta)$ in the form $$T(\theta) = \frac{K_m}{\theta^m}$$

Since $F(R)$ can be approximated by $$F(R) = C_N R^{M+2}$$

where $C_N$ is a constant and $(m + 2)$ is the power relationship selected and $N = m + 2$ Thus, for the second power relationship $m = o$ and $$T(\theta) = \frac{K_m}{\theta^o}$$

or $$T(\theta) = K_m$$

and that part of the total flux transmitted by the filter is constant with changes in $\theta$, the diffraction angle. Selecting the third power, $m = 1$ and $$T(\theta) = \frac{K_m}{\theta}$$

so that the part of the total flux transmitted is inversely proportional to the diffraction angle.

When $M = 2$ the fourth power relationship is obtained thus, $$T(\theta) = \frac{K_m}{\theta^2}$$

The 0° filter as shown in FIG. 2 consists of four sections. The first is in the area 70 for which a blowup is provided in FIG. 3. That area responds to diffracted light from the largest particles of the collection and is expanded in width to provide a response at detector 26 which will compensate for the diffracted light not passed in the area nearest the center of the mask where it is necessary to blank out a region adequate to prevent the transmission through the filter of the incident beam 12.

The second region 72 of the 0° filter is a pie shaped section as are the third region 74 and the fourth region 76. All of the regions may have the dimensions shown by way of example to provide the desired response characteristic when the particles range from 2 to 100 microns. The third and fourth regions are expanded with respect to the second region to compensate for the fact that the filter radius does not extend to infinity. Thus the third and fourth regions give enhanced response to compensate for the diffracted light which does not fall within the filter area.

The 125° filter is displaced clockwise 125° from the 0° filter, as shown in FIG. 2, and is designed to show one form of a spatial filter for producing a third power relationship between the particle radius and the flux transmitted. The innermost transparent region 80 of this filter is a pie shaped section and is shown in enlarged detail in FIG. 3. The second region 81 is a rectangular one and is so oriented that it is separated from the first and is connected with the third 82. The third region is likewise rectangular to give a third power response as described in the previous mentioned Wilcock application. A fourth region 83 is located near the periphery of the mask and connected to the third region.

The fourth region 83 deviates from the rectangular shape to compensate for the fact that the mask and hence the spatial filters do not extend to infinity and hence additional amounts of diffracted light are passed to provide a total flux at detector 26 which closely approximates what is lost in the range between the outer region of the filter and infinity.

The 235° filter is shown as comprising only a single region, namely a partial ring shaped section of transparency 84 near the center of the mask. It has the dimensions shown to provide a fourth power response to the particle radius so as to produce at detector 26 a signal $X_4$ from the flux transmitted by section 84.

What is claimed is:

1. Apparatus for measuring the mean of the area distribution, the mean of the volume distribution, and the standard deviation of the area distribution of a collection of particles comprising:

means for passing a light beam through said collection of particles, means for filtering the light diffracted from said beam through a first filter which transmits light flux diffracted from each particle proportional to the second power of its radius, means for filtering the light diffracted from said beam through a second filter which transmits light flux diffracted from each particle proportional to the third power of its radius, means for filtering the light diffracted from said beam through a third filter which transmits light flux diffracted from each particle proportional to the fourth power of its radius, means for producing a first, second and third signal ($X_2$, $X_3$ and $X_4$, respectively) in response to the integral of the light flux detected passing through the respective first, second and third filters due to all of the particles of said collection, means for calculating the mean of the area distribution ($M_A$) of the particles in said collection as a number proportional to the ratio $X_3/X_2$, means for calculating the mean of the volume distribution ($M_v$) of the particles in said collection as a number proportional to the ratio $X_4/X_3$, and means for calculating the standard deviation of the area distribution of the particles in said collection as the square root of the product $M_A(M_v - M_A)$.

2. Apparatus for measuring the mean of the area distribution of a collection of particles comprising:

means for passing a light beam through said collection of particles, means for filtering the light diffracted from said beam through a first filter which transmits light flux diffracted from each particle proportional to the second power of its radius, means for filtering the light diffracted from said beam through a second filter which transmits light flux diffracted from each particle proportional to the third power of its radius, means for producing a first and second signal ($X_2$ and $X_3$, respectively) in response to the integral of the light flux detected passing through the respective first and second filters due to all of the particles of said collection, means for calculating the mean of the area distribution ($M_A$) of the particles in said collection as a number proportional to the ratio $X_3/X_2$.

3. Apparatus for measuring the mean of the volume distribution of a collection of particles comprising:
   means for passing a light beam through said collection of particles,
   means for filtering the light diffracted from said beam through a first filter which transmits light flux diffracted from each particle proportional to the third power of its radius,
   means for filtering the light diffracted from said beam through a third spatial filter which transmits light flux diffracted from each particle proportional to the fourth power of its radius,
   means for producing a first and second signal ($X_3$ and $X_4$, respectively) in response to the integral of the light flux detected passing through the respective first and second filters due to all of the particles of said collection,
   means for calculating the mean of the volume distribution ($M_v$) of the particles in said collection as a number proportional to the ratio $X_4/X_3$.

4. Apparatus for continuously measuring the mean of the area distribution, the mean of the volume distribution, and the standard deviation of the area distribution of a flowing sample of fluid suspended particles comprising:
   means for directing a light beam through said sample;
   means for sequentially filtering the light diffracted by said particles said means including a rotating mask having spaced thereon radially oriented spatial filters including
      a first spatial filter which transmits light flux diffracted from each particle proportional to the second power of its radius,
      a second spatial filter which transmits light flux diffracted from each particle proportional to the third power of its radius,
      a third spatial filter which transmits light flux diffracted from each particle proportional to the fourth power of its radius, and
   a stationary chopping blade operable to block the diffracted light in sectors other than that occupied by that one of the spatial filters as sequentially selected;
   means for producing a first, second and third signal ($X_2$, $X_3$ and $X_4$, respectively) in response to the integral of the light flux detected passing through the respective first, second and third spatial filters due to all of the particles of said sample and summed over a predetermined time, and
   computer means for
   calculating the mean of the area distribution ($M_A$) of the particles in said sample as a number proportional to the ratio $X_3/X_2$,
   calculating the mean of the volume distribution ($M_v$) of the particles in said sample as a number proportional to the ratio $X_4/X_3$, and
   calculating the standard deviation of the area distribution of the particles in said sample as the square root of the product $M_A(M_v - M_A)$.

5. Apparatus for continuously measuring the mean of the area distribution of a flowing sample of fluid suspended particles comprising:
   means for directing a light beam through said sample;
   means for sequentially filtering the light diffracted by said particles said means including a rotating mask having spaced thereon radially oriented spatial filters including
      a first spatial filter which transmits light flux diffracted from each particle proportional to the second power of its radius,
      a second spatial filter which transmits light flux diffracted from each particle proportional to the third power of its radius, and
      a stationary chopping blade operable to block the diffracted light in sectors other than that occupied by that one of the spatial filters as sequentially selected;
   means for producing a first and second signal ($X_2$ and $X_3$, respectively) in response to the integral of the light flux detected passing through the respective first and second spatial filters due to all of the particles of said sample and summed over a predetermined time, and
   computer means for calculating the mean of the area distribution ($M_A$) of the particles in said sample as a number proportional to the average value of ratio $X_3/X_2$ over a predetermined period of time.

* * * * *